United States Patent
Schinazi et al.

(10) Patent No.: US 7,115,584 B2
(45) Date of Patent: Oct. 3, 2006

(54) HIV-1 MUTATIONS SELECTED FOR BY β-2',3'-DIDEHYDRO-2',3'-DIDEOXY-5-FLUOROCYTIDINE

(75) Inventors: Raymond F. Schinazi, Decatur, GA (US); Jennifer L. Hammond, Pittsburgh, PA (US); John W. Mellors, Pittsburgh, PA (US); Dennis C. Liotta, McDonough, GA (US)

(73) Assignee: Emory University, Atlanta, GA (US)

( * ) Notice: Subject to any disclaimer, the term of this patent is extended or adjusted under 35 U.S.C. 154(b) by 92 days.

(21) Appl. No.: 10/351,170

(22) Filed: Jan. 23, 2003

(65) Prior Publication Data

US 2004/0082552 A1   Apr. 29, 2004

Related U.S. Application Data

(63) Continuation of application No. 09/677,161, filed on Oct. 2, 2000, now Pat. No. 6,391,859, which is a continuation of application No. 09/488,874, filed on Jan. 21, 2000, now abandoned.

(60) Provisional application No. 60/116,773, filed on Jan. 22, 1999.

(51) Int. Cl.
*A61K 31/70* (2006.01)

(52) U.S. Cl. ............... 514/45; 514/49; 514/51

(58) Field of Classification Search ........... 514/45–51, 514/230.5, 261, 220, 231.5, 301, 473, 252, 514/253

See application file for complete search history.

(56) References Cited

U.S. PATENT DOCUMENTS

| | | | |
|---|---|---|---|
| 3,817,982 A | 6/1974 | Verheyden et al. | |
| 4,522,811 A | 6/1985 | Eppstein | |
| 4,725,442 A | 2/1988 | Haynes | |
| 4,788,181 A | 11/1988 | Driscoll et al. | |
| 4,891,225 A | 1/1990 | Langer | |
| 4,963,662 A | 10/1990 | Matthes et al. | |
| 5,034,394 A * | 7/1991 | Daluge | 514/263.4 |
| 5,196,438 A * | 3/1993 | Martin et al. | 514/311 |
| 5,366,972 A * | 11/1994 | Hargrave et al. | 514/220 |

(Continued)

FOREIGN PATENT DOCUMENTS

DE   1620047   3/1970

(Continued)

OTHER PUBLICATIONS (S) Romero et al., "Bis(heteroaryl)piperazine (BHAP) Reverse Transcriptase Inhibitors:" . . . , a Second Generation Clinical Candidate, Journal of Medicinal Chemistry, 36(10), 1505-1508 (May 14, 1993).*

(Continued)

*Primary Examiner*—S. Anna Jiang
*Assistant Examiner*—L. E. Crane
(74) *Attorney, Agent, or Firm*—Sherry M. Knowles, Esq.; King & Spalding LLP

(57) ABSTRACT

The present invention discloses a method for treating HIV that includes administering β-D-D4FC or its pharmaceutically acceptable salt or prodrug to a human in need of therapy in combination or alternation with a drug that induces a mutation in HIV-1 at a location other than the 70(K to N), 90 or the 172 codons of the reverse transcriptase region. Also disclosed is a method for using β-D-D4FC as "salvage therapy" to patients which exhibit drug resistance to other anti-HIV agents. β-D-D4FC can be used generally as salvage therapy for any patient which exhibits resistance to a drug that induces a mutation at other than the 70(K to N), 90 or the 172 codons.

19 Claims, 2 Drawing Sheets

β-D-D4FC

U.S. PATENT DOCUMENTS

| | | | |
|---|---|---|---|
| 5,409,810 A | | 4/1995 | Larder |
| 5,413,999 A | * | 5/1995 | Vacca et al. ............. 514/231.5 |
| 5,463,092 A | | 10/1995 | Hostetler |
| 5,484,926 A | * | 1/1996 | Dressman et al. .......... 546/114 |
| 5,489,593 A | * | 2/1996 | Palmer et al. ......... 514/253.09 |
| 5,496,935 A | | 3/1996 | Matthes et al. |
| 5,519,021 A | | 5/1996 | Young et al. |
| 5,561,120 A | | 10/1996 | Lin et al. |
| 5,563,142 A | * | 10/1996 | Palmer et al. ......... 514/253.09 |
| 5,585,397 A | * | 12/1996 | Tung et al. .................. 514/473 |
| 5,604,209 A | | 2/1997 | Ubasawa et al. |
| 5,627,160 A | | 5/1997 | Lin et al. |
| 5,631,239 A | | 5/1997 | Lin et al. |
| 5,703,058 A | * | 12/1997 | Schinazi et al. ............... 514/45 |
| 5,756,478 A | * | 5/1998 | Cheng et al. .................. 514/45 |
| 5,869,461 A | * | 2/1999 | Cheng et al. .................. 514/43 |
| 5,905,070 A | * | 5/1999 | Schinazi et al. ............... 514/49 |
| 6,232,300 B1 | * | 5/2001 | Schinazi et al. ............... 514/49 |
| 6,391,859 B1 | | 5/2002 | Schinazi et al. |

FOREIGN PATENT DOCUMENTS

| | | |
|---|---|---|
| EP | 0 409 227 A2 * | 1/1991 |
| EP | 0515156 B1 | 11/1992 |
| EP | 0519464 B1 | 12/1992 |
| NL | 8901258 | 12/1990 |
| WO | WO 91/06554 A1 | 5/1991 |
| WO | WO 91/09849 A1 * | 7/1991 |
| WO | WO91/09849 A1 * | 7/1991 |
| WO | WO 91/16333 A1 | 10/1991 |
| WO | WO 91/19727 A1 | 12/1991 |
| WO | WO 94/14456 A1 * | 7/1994 |
| WO | WO 94/27616 A1 * | 12/1994 |
| WO | WO 95/07287 A1 * | 3/1995 |
| WO | WO 96/22778 A1 | 8/1996 |
| WO | WO 96/28170 A1 | 9/1996 |
| WO | WO 99/66936 A1 | 12/1999 |

OTHER PUBLICATIONS

EPO Search Report for SN. 96 902772, Jul. 26, 1999.*

Romero et al., "Bis(heteroaryl)piperazine (BHAP) Reverse Transcriptase Inhibitors:" Structure-Activity Relationships of Novel Substituted Indole Analogues and the Identification of 1-[(5-Methansulfonamido-1H-indol-2-yl)-carbonyl]-4-[3-[(1-methylethyl)amino]pyridinyl]piperazine Monomethanesulfonate (U-90152SS), a Second Generation Clinical Candidate, *Journal of Medicinal Chemistry*, 36(10), 1505-1508 (May 14, 1993).*

Ajmera, S., et al., *J. Med. Chem.*, 27(1):11-14 (1984), Month of publication data not supplied or could not be determined from copy supplied.

Balzarini, J et al., *Biochem. And Biophys. Res. Comm.*, 164(3): (1989)(Nov. 15, 1989).

Chang, C., et al., *J. of Med. Chem.*, 267(20):13938-13942 (1992). (Jul. 15, 1992).

Chen, S H et al., Synthesis and comparative evaluation of two antiviral agents: beta-L-Fd4C and beta-D-Fd4C, *Bioorganic & Medicinal Chemistry Letters*, GB, Oxford, 8(22):3245-3250 (Nov. 17, 1998).

Choi, W. et al., *Biorganic & Med. Chem. Letters*, 3(4):693-696 (1993), Month of publication data not supplied or could not be determined from copy supplied.

Coe, P.L.. et al., *J. Flourine Chem.*, 69(1):19-24 (1994), Month of publication data not supplied or could not be determined from copy supplied.

Doong, S., et al., *Proc. Natl. Acad. Sci. (USA)*, 88:8495-8499 (1991). (Oct. 1991).

Frick, L.W., et al., *AntiMicrob. Agents and Chemotherapy*, 37(11):2285-2292 (Nov. 1993).

Hammer, S.M., "Advances in antiretroviral therapy and viral monitoring," *AIDS*, 10(3):s1-s11 (1996), Month of publication data not supplied or could not be determined from copy supplied.

Horwitz, J.P., et al., *Tetrah. Letters*, 1964(38):2725-2727, (1964), Month of publication data not supplied or could not be determined from copy supplied.

Hronowski, L.J.J., et al., *Can. J. Chem.*, 70(4):1162-1169 (1992), Month of publication data not supplied or could not be determined from copy supplied.

Izuta, S., et al., *Nucleic Acids Symp. Ser. (Symp. Nucleic Acids Chem., 13th)* 241-244 (1985)(Nov. 6, 1985).

Jeong, L.S., et al., *J. of Med. Chem.*, 36(2):181-195 (1993). (Jan. 22, 1993).

Khwaja, T.A., et al., *J. Med. Chem.*, 10(6):1066-1070 (1967). (Nov. 1967).

Kim, H.O., et al., *J. of Med. Chem.*, 36(5):519-528 (1993). (Mar. 5, 1993).

Larder, B.A., et al., *Science*, 243:1731-1734 (1989). (Mar. 31, 1989).

Mellors, J, W, et al., *Mol. Pharm.*, 41:446-451 (1992 ). (Jan. 1992).

Nunberg, J.H., et al., *J. Virol. I*, 65(9):4887-4892 (1991).(Sep. 1991).

Richman, D., et al., *Proc. Natl. Acad. Sci. (USA)*, 88:11241-11245 (1991). (Dec. 1991).

Schinazi, R.F. et al., *AntiMicrob. Agents and Chemotherapy*, 36(11):2423-2431 (1992). (Nov. , '92).

Schinazi, R.F. et al., *AntiMicrob. Agents and Chemotherapy*, 38(9):2172-2174 (1994). (Sep. 1994).

Schinazi, R.F., et al., "Mutations in retroviral genes associated with drug resistance: 2000-2001 update" *International Antiviral News* 8(5): 65-91 (2000). (May 2000).

Schinazi, R.F., et al., *Biochem. Pharma.*, 44(2):199-204 (1992), Month of publication data was not supplied or could not be determined from the copy supplied.

Shigeta, S., et al., *J. Infect. Dis.*, 163(2):270-275 (1991). (Feb. 1991).

Siddiqui, M.A., et al., *J. Med. Chem.*, 35(12):2195-2201 (1992), Month of publication data was not supplied or could not be determined from the copy supplied.

St. Clair, M.H., et al., *Science*, 253:1557-1559 (1991). (Sep. 27, 1991).

Van Aerschot, A., et al., *J. of Med. Chem.*, 33:1833-1839 (1990), Month of publication data was not supplied or could not be determined from the copy supplied.

Van Draanen, N.A. et al., *AntiMicrob. Agents and Chemotherapy* 38(4):868-871 (1994). (Apr. , 1994).

Wilson, L.J., et al., *Biorganic & Med. Chem. Letter*, 3(2):169-174 (1993), Month of publication data was not supplied or could not be determined from the copy supplied.

* cited by examiner

Figure 1 - Chemical Structure of β-D-D4FC
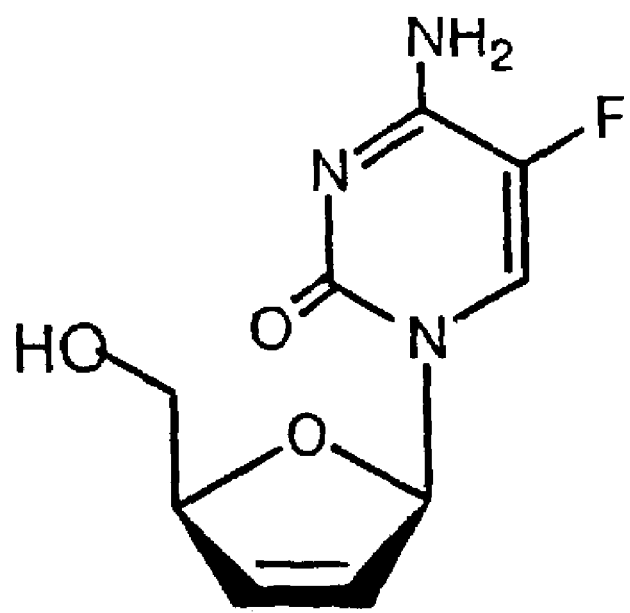
β-D-D4FC

Figure 2 - Selection of Virus with Reduced Sensitivity to D-D4FC

HIV-1 MUTATIONS SELECTED FOR BY β-2',3'-DIDEHYDRO-2',3'-DIDEOXY-5-FLUOROCYTIDINE

This application is a continuation of U.S. application Ser. No. 09/677,161, filed on Oct. 2, 2000, now U.S. Pat. No. 6,391,859, which is a continuation of U.S. application Ser. No. 09/488,874, filed on Jan. 21, 2000, now abandoned, which claims priority to U.S. Provisional Application Ser. No. 60/116,773, filed on Jan. 22, 1999, now abandoned.

This invention is partially funded by a grant from the United States National Institutes of Health under Grant No. 1R01-A1-41980-01. The U.S. government has certain rights to this invention.

BACKGROUND OF THE INVENTION

In 1983, the etiological cause of AIDS was determined to be the human immunodeficiency virus (HIV). In 1985, it was reported that the synthetic nucleoside 3'-azido-3'-deoxythymidine (AZT) inhibits the replication of human immunodeficiency virus. Since then, a number of other synthetic nucleosides, including 2',3'-dideoxyinosine (DDI), 2',3'-dideoxycytidine (DDC), 2',3'-dideoxy-2',3'-didehydrothymidine (D4T), cis-2hydroxymethyl-5-(5-fluorocytosin-1-yl)-1,3-oxathiolane (FTC), (−)-cis-2-hydroxymethyl-5-(cytosin-1-yl)-1,3-oxathiolane (3TC), have been proven to be effective against HIV. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enzyme reverse transcriptase.

It has been recognized that drug-resistant variants of HIV can emerge after prolonged treatment with an antiviral agent. Drug resistance most typically occurs by mutation of a gene that encodes for an enzyme used in viral replication, and most typically in the case of HIV, reverse transcriptase, protease, or DNA polymerase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous pressures on the virus. One cannot predict, however, what mutations will be induced in the HIV-1 genome by a given drug, whether the mutation is permanent or transient, or how an infected cell with a mutated HIV-1 sequence will respond to therapy with other agents in combination or alternation. This is exacerbated by the fact that there is a paucity of data on the kinetics of drug resistance in long-term cell cultures treated with modern antiretroviral agents.

HIV-1 variants resistant to 3'-azido-3'-deoxythymidine (AZT), 2',3'-dideoxyinosine (DDI) or 2',3'-dideoxycytidine (DDC) have been isolated from patients receiving long term monotherapy with these drugs (Larder B A, Darby G, Richman D D. *Science* 1989;243:1731–4; St Clair M H, Martin J L, Tudor W G, et al. *Science* 1991;253:1557–9; St Clair M H, Martin J L, Tudor W G, et al. *Science* 1991; 253:1557–9; and Fitzgibbon J E, Howell R M, Haberzettl C A, Sperber S J, Gocke D J, Dubin D T. *Antimicrob Agents Chemother* 1992;36:153–7). Mounting clinical evidence indicates that AZT resistance is a predictor of poor clinical outcome in both children and adults (Mayers D L. Lecture at the Thirty-second Interscience Conference on Antimicrobial Agents and Chemotherapy. (Anaheim, Calif. 1992); Tudor-Williams G, St Clair M H, McKinney R E, et al. *Lancet* 1992;339:15–9; Ogino M T, Dankner W M, Spector S A. *J Pediatr* 1993;123:1–8; Crumpacker C S, D'Aquila R T, Johnson V A, et al. Third Workshop on Viral Resistance. (Gaithersburg, Md. 1993); and Mayers D, and the RV43 Study Group. Third Workshop on Viral Resistance. (Gaithersburg, Md. 1993)). The rapid development of HIV-1 resistance to nonnucleoside reverse transcriptase inhibitors (NNRTIs) has also been reported both in cell culture and in human clinical trials (Nunberg J H, Schleif W A, Boots E J, et al. *J Virol* 1991 ;65(9):4887–92; Richman D, Shih C K, Lowy I, et al. *Proc Natl Acad Sci (USA)* 1991;88 :11241–5; Mellors J W, Dutschman G E, Im G J, Tramontano E, Winkler S R, Cheng Y C. *Mol Pharm* 1992;41:446–51; Richman D D and the ACTG 164/168 Study Team. Second International HIV-1 Drug Resistance Workshop. (Noordwijk, the Netherlands. 1993); and Saag M S, Emini E A, Laskin O L, et al. *N Engl J Med* 1993;329:1065–1072). In the case of the NNRTI L'697,661, drug-resistant HIV-1 emerged within 2–6 weeks of initiating therapy in association with the return of viremia to pretreatment levels (Saag M S, Emini E A, Laskin O L, et al. *N Engl J Med* 1993;329:1065–1072). Breakthrough viremia associated with the appearance of drug-resistant strains has also been noted with other classes of HIV-1 inhibitors, including protease inhibitors (Jacobsen H, Craig C J, Duncan I B, Haenggi M, Yasargil K, Mous J. Third Workshop on Viral Resistance. (Gaithersburg, Md. 1993)). This experience has led to the realization that the potential for HIV-1 drug resistance must be assessed early on in the preclinical evaluation of all new therapies for HIV-1.

2',3'-Dideoxy-2',3'-didehydro-5-fluorocytidine (D4FC) is a known compound. European Patent Application Publication No. 0 409 227 A2 filed by Ajinomoto Co., Inc., discloses β-D-D4FC (Example 2) and its use to treat hepatitis B. Netherlands Patent No. 8901258 filed by Stichting Rega V. Z. W. discloses generally 5-halogeno-2',3'-dideoxy-2',3'-didehydrocytidine derivatives for use in treating HIV and hepatitis B ("HBV"). U.S. Pat. No. 5,703,058 discloses a method for the treatment of HIV and HBV infection that includes administering an effective amount of β-L-D4FC in combination or alternation with cis-2-hydroxymethyl-5-(5-fluorocytosin-1-yl)-1,3-oxathiolane, cis-2-hydroxymethyl-5-(cytosin-1-yl)-1,3-oxathiolane, 9-[4-(hydroxymethyl)-2-cyclopenten-1-yl)-guanine (carbovir), 9-[(2-hydroxyethoxy)methyl]guanine (acyclovir), interferon, 3'-deoxy-3'-azidothymidine (AZT), 2',3'-dideoxyinosine (DDI), 2',3'-dideoxycytidine (DDC), (−)-2'-fluoro-5-methyl-β-L-arauridine (L-FMAU) or 2',3'-didehydro-2',3'-dideoxythymidine (D4T). U.S. Pat. No. 5,905,070 discloses a method for the treatment of HIV and HBV infection that includes administering an effective amount of β-D-D4FC in combination or alternation with cis-2-hydroxymethyl-5-(5-fluorocytosin-1-yl)-1,3-oxathiolane, cis-2-hydroxymethyl-5-(cytosin-1-yl)-1,3-oxathiolane, 9-[4-(hydroxymethyl)-2-cyclopenten-1-yl)-guanine (carbovir), 9-[(2-hydroxyethoxy)methyl]guanine (acyclovir), interferon, 3'-deoxy-3'-azidothymidine (AZT), 2',3'-dideoxyinosine (DDI), 2',3'-dideoxycytidine (DDC), (−)-2'-fluoro-5-methyl-β-L-arauridine (L-FMAU) or 2',3'-didehydro-2',3'-dideoxythymidine (D4T).

It is an object of the present invention to determine the optimal administration of β-D-D4FC for the treatment of HIV.

It is another object of the present invention to provide a method and composition that includes β-D-D4FC for the treatment of patients infected with HIV that exhibits advantageous or improved pharmacokinetic, biodistribution, metabolic, resistance or other parameters over administration of β-D-D4FC alone.

It is yet another object of the present invention to provide a method and composition for the treatment of patients infected with HIV in which β-D-D4FC is administered in combination or alternation with a second compound that acts synergistically with β-D-D4FC against the virus.

It is still another object of the present invention to provide a method and composition for the treatment of patients infected with a drug resistant form of HIV.

It is another object of the present invention to provide a method and kit to assess how to best administer β-D-D4FC.

SUMMARY OF THE INVENTION

It has been discovered that β-D-D4FC induces mutations in HIV-1 at the 70(K to N), 90 and the 172 codons of the reverse transcriptase region of the virus. Based on this discovery, a method for treating HIV is provided that includes administering β-D-D4FC or its pharmaceutically acceptable salt or prodrug to a human in need of therapy in combination or alternation with a drug that induces a mutation in HIV-1 at a location other than the 70(K to N), 90 or the 172 codons of the reverse transcriptase region. This invention can be practiced by referring to published mutation patterns for known anti-HIV drugs, or by determining the mutation pattern for a new drug.

Based on this discovery, a method for using β-D-D4FC as "salvage therapy" to patients which exhibit drug resistance to other anti-HIV agents is also provided. It has been discovered that β-D-D4FC is not significantly cross-resistant to AZT, DDC, DDI, D4T, 3TC, (–)-FTC or β-L-D4FC. In contrast, β-L-D4FC rapidly induces a mutation at codon 184 (methionine to valine), resulting in a high level of resistance to 3TC and FTC. β-D-D4FC can be used generally as salvage therapy for any patient which exhibits resistance to a drug that induces a mutation at other than the 70(K to N), 90 or the 172 codons.

The invention disclosed herein more generally includes at least the following embodiments:

(i) A method for treating an HIV infection in a human comprising administering an effective amount of β-D-D4FC or its pharmaceutically acceptable prodrug or salt to the human, optionally in a pharmaceutically acceptable carrier, in combination or alternation with a drug that induces a mutation in HIV-1 at a location other than the 70(K to N), 90 or 172 codon of the reverse transcriptase region, and which is other than cis-2-hydroxymethyl-5-(5-fluorocytosin-1-yl)-1,3-oxathiolane, cis-2-hydroxymethyl-5-(cytosin-1-yl)-1,3-oxathiolane, 9-[4-(hydroxymethyl)-2-cyclopenten-1-yl]-guanine (carbovir), 9-[(2-hydroxyethoxy)methyl]guanine (acyclovir), interferon, 3'-deoxy-3'-azido-thymidine (AZT), 2',3'-dideoxyinosine (DDI), 2',3'-dideoxycytidine (DDC), (–)-2'-fluoro-5-methyl-β-L-ara-uridine (L-FMAU) or 2',3'-didehydro-2',3'-dideoxythymidine (D4T).

(ii) A method for treating an HIV infection in a human comprising administering an effective amount of β-D-D4FC or its pharmaceutically acceptable salt to the human, optionally in a pharmaceutically acceptable carrier, in combination or alternation with a drug that induces a mutation in HIV-1 at codon 70 from K to N (i.e., lysine to asparagine), a mutation at codon 90 from V to I (i.e., valine to isoleucine), or mutation at codon 172 from R to K (i.e., arginine to lysine) of the reverse transcriptase region, and which is other than cis-2-hydroxymethyl-5-(5-fluorocytosin-1-yl)-1,3-oxathiolane, cis-2-hydroxymethyl-5-(cytosin-1-yl)-1,3-oxathilane, 9-[4-(hydroxymethyl)-2-cyclopenten-1-yl]-guanine (carbovir), 9-[(2-hydroxyethoxy)methyl]guanine (acyclovir), interferon, 3'-deoxy-3'-azido-thymidine (AZT), 2',3'-dideoxyinosine (DDI), 2',3'-dideoxycytidine (DDC), (–)-2'-fluoro-5-methyl-β-L-ara-uridine (L-FMAU) or 2',3'-didehydro-2',3'-dideoxythymidine (D4T).

(iii) A method for treating a patient infected with a strain of HIV virus that is resistant to 3TC, comprising administering an effective amount of β-D-D4FC or its pharmaceutically acceptable prodrug or salt to the patient optionally in a pharmaceutically acceptable carrier.

(iv) A method for treating a patient infected with a strain of HIV virus that is resistant to AZT, comprising administering an effective amount of β-D-D4FC or its pharmaceutically acceptable prodrug or salt to the patient optionally in a pharmaceutically acceptable carrier.

(v) A method for treating a patient infected with a strain of HIV virus that is resistant to cis-2-hydroxymethyl-5-(5-fluorocytosin-1-yl)-1,3-oxathiolane, comprising administering an effective amount of β-D-D4FC or its pharmaceutically acceptable prodrug or salt, to the patient optionally in a pharmaceutically acceptable carrier.

(vi) A method for treating a patient infected with a strain of HIV virus that is resistant to cis-2-hydroxymethyl-5-(cytosin-1-yl)-1,3-oxathiolane, comprising administering an effective amount of β-D-D4FC, or its pharmaceutically acceptable prodrug or salt, to the patient optionally in a pharmaceutically acceptable carrier.

(vii) A method for treating a patient infected with a strain of HIV virus that is resistant to 2',3'-didehydro-2',3'-dideoxythymidine (D4T), comprising administering an effective amount of β-D-D4FC, or its pharmaceutically acceptable prodrug or salt, to the patient optionally in a pharmaceutically acceptable carrier.

(viii) A method for treating a patient infected with a strain of HIV virus that is resistant to 2',3'-dideoxyinosine (DDI), comprising administering an effective amount of β-D-D4FC, or its pharmaceutically acceptable prodrug or salt, to the patient optionally in a pharmaceutically acceptable carrier.

(ix) A method for treating a patient infected with a strain of HIV virus that is resistant to 2',3'-dideoxycytidine (DDC), comprising administering an effective amount of β-D-D4FC, or its pharmaceutically acceptable prodrug or salt, to the patient optionally in a pharmaceutically acceptable carrier.

(x) A method for treating a patient infected with HIV comprising administering an effective amount of β-D-D4FC or its prodrug or pharmaceutically acceptable salt in combination or alternation with an effective amount of (S)-6-chloro-4-cyclopropylethynyl-4-trifluoromethyl-1,4-dihydro-2H-3,1-benzoxazin-2-one (SUSTIVA, see U.S. Pat. No. 5,519,021).

The disclosed combination, alternation, or salvage regiments are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

BRIEF DESCRIPTION OF THE FIGURES

FIG. 1 is a drawing of β-D-D4FC.

FIG. 2 is a graph of the concentration of β-D-D4FC in micromolar versus the percent inhibition of p24 antigen production. The figure illustrates the selection of virus with reduced sensitivity to β-D-D4FC.

DETAILED DESCRIPTION OF THE INVENTION

I. Definitions

As used herein, the term "resistant virus" refers to a virus that exhibits a three, and more typically, five or greater fold increase in $EC_{50}$ compared to naive virus in a constant cell line, including, but not limited to peripherial blood mononuclear cells (PBMCs), or MT2 or MT4 cells.

The term D-D4FC is used interchangeably with the term β-D-D4FC below.

As used herein, the term "substantially pure" or "substantially in the form of one optical isomer" refers to a nucleoside composition that includes at least 95% to 98%, or more, preferably 99% to 100%, of a single enantiomer of that nucleoside. In a preferred embodiment, β-D-D4FC is administered in substantially pure form for any of the disclosed indications.

As used herein, the term "prodrug" refers to the 5' and $N^4$ acylated, alkylated, or phosphorylated (including mono, di, and triphosphate esters as well as stabilized phosphates and phospholipid ) derivatives of D-D4FC. In one embodiment, the acyl group is a carboxylic acid ester in which the non-carbonyl moiety of the ester group is selected from straight, branched, or cyclic alkyl, alkoxyalkyl including methoxymethyl, aralkyl including benzyl, aryloxyalkyl including phenoxymethyl, aryl including phenyl optionally substituted by halogen, alkyl, alkyl or alkoxy, sulfonate esters such as alkyl or aralkyl sulphonyl including methanesulfonyl, trityl or monomethoxytrityl, substituted benzyl, trialkylsilyl, or diphenylmethylsilyl. Aryl groups in the esters optimally comprise a phenyl group. The alkyl group can be straight, branched or cyclic and is preferably $C_1$ to $C_{18}$.

As used herein, the term "pharmaceutically acceptable salts" refers to pharmaceutically acceptable salts which, upon administration to the recipient, are capable of providing directly or indirectly, β-D-D4FC, or that exhibit activity themselves.

The abbreviations of amino acids used herein are described in Table 1.

TABLE 1

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU GAC GAU |
| Glutamic Acid | Glu | E | GAA GAG |
| Phenylalanine | Phe | F | UUC UUU |
| Clycine | Gly | G | GGA GCG GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG GUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |

TABLE 1-continued

| Amino Acids | | | Codons |
|---|---|---|---|
| Valine | Val | V | GUA GUC GUG GUU |
| Tryptophan | Trp | W | UGG |
| Tyrosine | Tyr | Y | UAC UAU |

II. Mutations in HIV-1 Reverse Transcriptase Selected for by β-D-D4FC

Both the D- and L-enantiomers of β-2',3'-didehydro-2',3'-dideoxy-5-fluorocytidine (D4FC) are potent and selective inhibitors of HIV-1, although the D-enantiomer is more selective. The in vitro development of resistance to D-D4FC was assessed by serial passage of HIV-$I_{LA1}$ in MT-2 cells and peripheral blood mononuclear cells (PBMC) in the presence of increasing concentrations of drug. Variants resistant to D-D4FC arose only after prolonged exposure to the drug. Virus obtained after 20 passages in MT-2 cells exhibited 5.3-fold resistance to D-D4FC. Resistant virus could not be isolated in PBMC despite multiple attempts. DNA sequencing of RT from virus selected in MT-2 cells revealed two mutations: K65R and V179D. The selection of D-D4FC resistant virus was repeated in MT-2 cells and variants exhibiting 19.3-fold resistance encoded three novel RT mutations: K70N, V901 and R172K. A K65R recombinant HIV-$1_{LA1}$ virus exhibited 3.9-fold resistance to D-D4FC. VI 79D, a mutation conferring resistance to nonnucleoside RT inhibitors, is most likely compensatory for K65R. The role of the other mutations in resistance to D-D4FC was also evaluated by construction of recombinant virus with single and multiple mutations, however, none of the recombinants tested demonstrated >2-fold resistance.

Materials and Methods

Chemicals. D-D4FC was synthesized in one of our laboratories as described previously (Shi et al, 1999). It was prepared as 10 mM stock solutions in sterile water and stored at −20° C. The compound was thawed and diluted to the desired concentration immediately before use.

Cells. MT-2 cells (AIDS Research and Reference Reagent Program, National Institute of Allergy and Infectious Diseases, National Institutes of Health, contributed by D. Richman) were cultured in RPMI 1640 (Whittaker M. A., Bioproducts, Walkersville, Md.) supplemented with 10% fetal bovine serum, 10 mM HEPES buffer, penicillin (50 IU/ml) and streptomycin (50 μg/ml).

Viruses. HIV-$1_{LA1}$, a molecularly cloned clinical isolate, was used both as the starting virus for the resistance selection as well as for the generation of recombinant mutants. Stock preparations of HIV-$1_{LA1}$ were prepared by electrophorating 5–10 jig of proviral plasmid DNA into $1.3\times10^7$ MT-2 cells. At peak viral cytopathic effect (generally 7 days post transfection), the supernatant from infected cultures was collected, aliquoted and stored at −80° C. until use. Virus preparations were titered by threefold endpoint dilution in MT-2 cells, and the $TCID_{50}$ was calculated with the Reed and Muench equation.

Selection of resistant virus. Prior to starting the selection of D-D4FC resistant virus, the starting virus (HIV-$1_{LA1}$) was passaged as cell-free virus for 10 cycles in MT-2 cells in the absence of drug. D-D4FC resistant virus was selected by serially passaging HIV-$1_{LA1}$ in MT-2 cells in the presence of gradually increasing concentrations of D-D4FC. The selection for D-D4FC resistant virus was conducted twice. Selection was initiated by inoculating $1\times10^6$ MT-2 cells with 0.01 mol of virus. At peak viral cytopathic effect (4–7 days post infection), supernatant from the infected cultures was collected and 0.1–0.3 ml were subsequently used to initiate another cycle of infection. Supernatant was also aliquoted and stored at −80° C. for characterization of selected virus. Virus was passaged at least three times at each concentration, the number of cycles at any given concentration of drug being dependent on the ability of virus to grow at the particular concentration of D-D4FC. During the first selection procedure, virus was passaged once in the absence of drug prior to increasing the drug concentration (Table 2). As a control, virus was also passaged in parallel in the absence of drug. The first selection was initiated at 0.75 µM and gradually increased to 4.0 µM during the course of 37 cycles of cell-free passage. The second selection was initiated at 0.2 µM and gradually increased to 6.2 µM during the course of 27 cycles of cell-free passage (Table 2).

TABLE 2

| Selection #1 | | Selection #2 | |
|---|---|---|---|
| Passage Number | [D-Fd4C] µM | Passage Number | [D-Fd4c] µM |
| 1–2 | 0.75 | 1–3 | 0.2 |
| 3–4 | 1.5 | 4–6 | 0.4 |
| 5 | 1.0 | 7–9 | 0.8 |
| 6 | 0 | 10–12 | 1.6 |
| 7–9 | 1.5 | 13 | 3.2 |
| 10–12 | 2.0 | 14–16 | 1.6 |
| 13–16 | 3.0 | 17–19 | 3.2 |
| 17 | 0 | 20–22 | 4.8 |
| 18–20 | 4.5 | 23–25 | 6.2 |
| 21 | 0 | 26 | 12.0 |
| 22–35 | 4.5 | 27 | 6.2 |
| 36–38 | 1.0 | | |
| 39–41 | 2.0 | | |
| 42–43 | 4.0 | | |

Antiviral susceptibility assays. Virus susceptibility to D-D4FC was measured by measuring percent inhibition of p24 antigen production. Briefly, MT-2 cells (1×10$^5$ cells/ml) were infected with virus at a moi of 0.01 in the presence of serial D-D4FC dilutions. Each dilution was tested in triplicate. Culture supernatants were harvested day 7 post infection and assayed for p24 antigen production using a commercial assay (DuPont, NEN Products, Wilmington, Del.). Virus susceptibility is expressed as the concentration of drug required to inhibit production of p24 antigen by 50% (EC$_{50}$).

DNA sequencing of selected virus reverse transcriptase. The viral RNA (vRNA) from selected virus was isolated using TRIzol Reagent (GibcoBRL, Grand Island, N.Y.). The full-length RT coding region was amplified by RT-PCR. The PCR product was subsequently purified using Wizard PCR preps (Promega, Madison, Wis.) and sequenced.

Production of mutant recombinant HIV-1. Mutant RT was generated using the Altered SitesII in vitro Mutagenesis System (Promega, Madison, Wis.). Mutagenesis was carried out on HIV-1$_{LAI}$, RT cloned into a mutagenesis vector (PALTER, Promega). The presence of the desired mutation was determined by direct sequencing of the RT gene. The mutant RT was subsequently ligated into the pxxHIV-1$_{LAI}$ vector. Stocks of mutant virus were then prepared by electrophorating 5–10 µg of DNA into 1.3×10$^7$ MT-2 cells as described above.

Results and Discussion

Phenotyping of resistant virus. Virus resistant to D-D4FC was selected after 37 (selection #1) and 20 (selection #2) cycles of infection in MT-2 cells. Assessment of the D-D4FC susceptibility of virus from selection #1 passage 37 (p37 D-D4FC#1) demonstrated that p37 D-D4FC#1 is 19.4-fold less sensitive to D-D4FC than wild type as demonstrated by an increase in the EC$_{50}$, from 0.21 µM to 4.07 µM (FIG. 2, Table 3). Assessment of the D-D4FC susceptibility of virus from selection #2 passage 20 (p20 D4FC #2) demonstrated that p20 D-D4FC#2 is 5.3-fold less sensitive to D-D4FC than wild type as demonstrated by an increase in the EC$_{50}$ from 0.21 µM to 1.1 µM (FIG. 2, Table 3).

Genotyping of resistant virus. vRNA from p37 D-D4FC#1 and p20 D-D4FC#2 was isolated and subjected to amplification by RT-PCR. Sequencing of the PCR product revealed the presence of three novel mutations in p37 D-D4FC#I: K70N (AAA→4AAT), V90I (GTT→ATT) and RI 72K (AGA→AAA) (Table 2). Two different mutations were identified in p20 D-D4FC#2: K65R (AAA→AGA) and V179D (GTT→GAT) (Table 3). No other mutations were found in the RT genes from these viruses (from amino acids 8–330). Additionally, no mutations were found in the control viruses passaged in parallel in the absence of drug.

The isolation of D-D4FC resistant viruses with different associated mutations could be the result of the different selection techniques used to isolate D-D4FC resistant virus. In selection #1, the selective pressure was removed for one cycle of infection prior to increasing the drug concentration. This was not done during the second selection procedure. Additionally, the starting concentration of D-D4FC used for each of the selection procedures varied approximately 3-fold. A much higher starting concentration of drug was used for selection #1 (0.75 µM). These two differences are likely the cause of the different mutations seen in the selected viruses.

Mutant recombinant HIV-1. Mutant recombinant HIV-1 containing the mutations identified in the selected viruses were generated via site directed mutagenesis. Table 4 lists each of the mutant recombinant viruses generated as well as the corresponding EC$_{50}$. While the xxHIV-1$_{LAI}$, K65R virus demonstrated a 3.9-fold decrease in susceptibility to D-D4FC, none of the other viruses showed >3.0 fold resistance. It should be noted, however, that the triple mutant (xxHIV-1$_{LAI}$, K70N/V90I/RI72K) did not grow well, and this could be the cause of the inability to reproduce the resistance observed in the in vitro selected virus.

TABLE 3

Susceptibility and Associated Mutations of D-D4FC Selected Virus in MT-2 Cells

| Virus | EC$_{50}$ (µM) | Fold Resistance | Mutations from Baseline |
|---|---|---|---|
| HIV-1$_{LAI}$p0 | 0.21 | — | — |
| HIV-1p37 D-Fd4C#1 | 4.07 | 19.4 | K70N V90I R172K |
| HIV-1p20 D-Fd4C#2 | 1.11 | 5.3 | K65R V179D |

TABLE 4

D-D4FC Susceptibility of Recombinant HIV-1 in MT-2 Cells

| Virus | EC$_{50}$ | Fold Resistance |
|---|---|---|
| xxLAI | 0.32 | — |
| xxK65R | 1.24 | 3.9 |
| xxLAI | 0.17 | — |
| xxK70N | 0.24 | 1.4 |
| xxV90I | 0.25 | 1.5 |
| xxLAI | 0.28 | — |
| xxR172K | 0.23 | 0.8 |
| xxV90I/R172K | 0.36 | 1.3 |
| xxLAI | 0.13 | — |
| xxK70N/V90I/R172K | 0.056 | 0.4 |

Table 5 provides the median effective concentration and combinations index (C.I.) values for D-D4FC alone and in combination with AZT and D4T in acutely infected human PBM cells (Day6). Table 6 describes the effect of β-D and β-L-D4FC against HIV-1 and cloned viruses I human PBM cells.

art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the admin-

TABLE 5

Median effective concentration and combinations index (C.I.) values for D-D4FC alone and in combination with AZT and D4T in acutely infected human PBM cells (Day 6).

| Treatment (drug ratio) | Parameter[a] | | | | C.I. at $F_a$[b] of | | | |
|---|---|---|---|---|---|---|---|---|
| | m ± SE | $EC_{50}$ (μM) | $EC_{90}$ (μM) | r | 0.50 | 0.75 | 0.90 | 0.95 |
| D-D4FC | 0.95 ± 0.17 | 0.0076 | 0.078 | 0.97 | | | | |
| AZT | 0.96 ± 0.17 | 0.0033 | 0.032 | 0.98 | | | | |
| D4T | 0.82 ± 0.16 | 0.015 | 0.22 | 0.95 | | | | |
| D-D4FC/AZT (100:1) | 0.65 ± 0.09 | 0.0012 | 0.035 | 0.96 | 0.164 ± 0.134 *0.163 ± 0.120* | 0.276 ± 0.233 *0.274 ± 0.215* | 0.465 ± 0.407 *0.460 ± 0.384* | 0.664 ± 0.598 *0.654 ± 0.571* |
| D-D4FC/D4T (5:1) | 0.86 ± 0.11 | 0.0087 | 0.11 | 0.98 | 1.14 *1.045* | 1.25 *1.154* | 1.38 *1.276* | 1.47 ± 1.44 *1.37 ± 1.27* |

[a] m is the slope ± S.E., $EC_{50}$ is the median effective concentration, and r is the correlation coefficient, as determined from the median effect plot.
[b] C.I. <1, equal to 1 or >1 indicates synergy, additivity and antagonism.
$F_a$ is a componet of the median effect equation referring to the fraction of the system affected (e.g., 0.50 means the C.I. at a 50% reduction of RT activity).
C.I. values were determined for a mutually non-exclusive interaction (values in italics are for mutually exclusive interaction, which is less vigorous).

TABLE 6

Effect of β-D- and β-L-D4FC against HIV-1 and cloned viruses in human PBM cells

| | β-D-D4FC | | | | β-L-D4FC | | | |
|---|---|---|---|---|---|---|---|---|
| Virus | $EC_{50}$, μM | $EC_{90}$, μM | $FI_{50}$ | $FI_{90}$ | $EC_{50}$, μM | $EC_{90}$, μM | $FI_{50}$ | $FI_{90}$ |
| HIV-1$_{LAV}$ | 0.22 | 1.32 | — | — | 0.034 | 0.16 | — | — |
| xxBRU$_{PITT}$ | 0.065 | 0.46 | — | — | 0.025 | 0.088 | — | — |
| M184V$_{PITT}$ | 0.14 | 1.04 | 2 | 2 | 3.66 | 14.3 | 146 | 163 |
| 4X AZT$_{PITT}$ (67N, 70R, 215Y, 219Q) | 0.072 | 0.46 | 1 | 1 | 0.016 | 0.11 | 1 | 1 |
| T215Y$_{PITT}$ | 0.067 | 0.35 | 1 | 1 | 0.0047 | 0.03 | 0.2 | 0.3 |
| M184V/T215Y$_{PITT}$ | 0.057 | 0.47 | 1 | 1 | 8.3 | 74.6 | 332 | 848 |
| 215/41$_{PITT}$ | 0.13 | 0.49 | 2 | 1 | 0.018 | 0.066 | 1 | 1 |
| 4xM184V$_{PITT}$[a] (184V, 67N, 70R, 215Y, 219Q) | 0.045 | | 0.2 | | >3.3 | | >47 | |
| G2-2$_{PITT}$[a] (103N, 41L, 184V, 210W, others[b]) | 0.04 | | 0.2 | | >3.3 | | >47 | |
| L-D4FC-res. (25 μM) | ND | ND | ND | ND | 7.56 | 33.3 | 222 | 208 |

$FI_{50}$ = $EC_{50}$ data from resistant virus $EC_{50}$ data from HIV-1$_{LAV}$ or xxBRU$_{PITT}$.
$FI_{90}$ = $EC_{90}$ data from resistant virus $EC_{90}$ data from HIV-1$_{LAV}$ or xxBRU$_{PITT}$.
Values in bold indicate FI > 10.
[a] In MT-2 cells: Cortesey of Dr. J. Mellors (Pittsburgh)
[b] Additional mutations: 203D, 207A, 211K, 214F, 245M, 277N, 283I, 284K, 200D, 311R

III. Combination or Alternation HIV-Agents

In general, during alternation therapy, an effective dosage of each agent is administered serially, whereas in combination therapy, an effective dosage of two or more agents are administered together. In alternation therapy, for example, one or more first agents can be administered in an effective amount for an effective time period to treat the viral infection, and then one or more second agents substituted for those first agents in the therapy routine and likewise given in an effective amount for an effective time period.

The dosages will depend on such factors as absorption, biodistribution, metabolism and excretion rates for each drug as well as other factors known to those of skill in the istration of the compositions. Examples of suitable dosage ranges for anti-HIV compounds, including nucleoside derivatives (e.g. AZT, D4T, DDI, and 3TC) or protease inhibitors, for example, nelfinavir and indinavir, can be found in the scientific literature and in the Physicians Desk Reference. Many examples of suitable dosage ranges for other compounds described herein are also found in public literature or can be identified using known procedures. These dosage ranges can be modified as desired to achieve a desired result.

In one preferred embodiment, D-D4FC is administered in combination with a protease inhibitor. In particular embodiments, D-D4FC is administered in combination or alternation with indinavir (Crixivan), nelfinavir ([3S-[2(2S*,3S*), 3-alpha,4-a-beta,8a-beta-]]-N-(1,1-dimethylethyl) decahydro-2-)2-hydrozy-3-[(3-hydrozy-2-methylbenzoyl) amino]-4-(phenylthio)butyl]-3-isoquinolincarboxamide mono-methanesulfonate) (Viracept), saquinavir (Invirase), or 141W94 (amprenavir; (S)-tetrahydrofuran-3-yl-N-[(1S, 2R)-3-[N-[(4-aminophenyl)sulfonyl]-N-isobutylamino]-1-benzyl-2-hydroxypropyl]carbamate; or (S)-6-chloro-4-(cyclopropylethynyl)-1,4-dihydro-4-(trifluoromethyl)-2H-3,1-benzoxazin-2-one (efavirenz).

In another preferred embodiment, D-D4FC is administered in combination or alternation with a nucleoside analog, including abacavir (1592U89) which is (1S,4R)-4-[2-amino-6-cyclopropyl-amino)-9H-purin-9-yl]-2-cyclopentene-1-methanol succinate.

In another embodiment, D-D4FC is administered in combination with a nonnucleoside reverse transcriptase inhibitor such as DMP-266 ((S)-6-chloro-4-cyclopropylethynyl-4-trifluoromethyl-1,4-dihydro-2H-3,1-benzoxazin-2-one (SUSTIVA, see U.S. Pat. No. 5,519,021); delavirdine, (1-[3-(1-methyl-ethyl)amino]-2-pyridinyl-4-[[5-[(methylsulfonyl) amino]-1H-indol-2-yl]carbonyl]-,monoethanesulfonate), nevirapine, or delarvirdine.

In other embodiments, D-D4FC is administered in combination or alternation with an HIV-integrase inhibitor or a chemokine inhibitor.

II. Analysis of D-D4FC Induced Mutation of HIV Genome

Methods and kits similar to those described in U.S. Pat. No. 5,409,810 to Larder et al, for AZT, but based on the mutation profile for D-D4FC, can be used to analyze for the presence of D-D4FC induced mutations and thus form part of the invention presented herein. In addition to incorporating the Larder patent by reference in its entirety, these techniques are set out below.

In one aspect of the invention there is provided a method of assessing the sensitivity of an HIV-1 sample to D-D4FC, which includes:

(i) isolating nucleic acid from the sample,
(ii) hybridizing an oligonucleotide to the nucleic acid, the oligonucleotide being complementary to a region of the wild-type DNA sequence (or its corresponding RNA) or to a region of the mutant DNA sequence (or its corresponding RNA);
(iii) attempting polymerization of the nucleic acid from the 3'-end of the oligonucleotide,
(iv) ascertaining whether or not an oligonucleotide primer extended product is present.

It is possible to use genomic DNA or RNA isolated from HIV-1 samples in this methodology. Suitable cells for supporting the growth of HIV-1 isolate are incubated for a period of time. The cells are recovered by centrifugation. DNA can then be isolated by digestion of the cells with proteinase K in the presence of EDTA and a detergent such as SDS, followed by extraction with phenol.

Well-known extraction and purification procedures are available for the isolation of DNA from a sample. RNA can be isolated using the following methodology. Suitable cells are being infected and incubated for a period of time. The cells are recovered by centrifugation. The cells are resuspended in an RNA extraction buffer followed by digestion using a proteinase digestion buffer and digestion with proteinase K. Proteins are removed in the presence of a phenol/chloroform mixture. RNA can then be recovered following further centrifugation steps. (Maniatis, T., et al, Molecular Coning, A laboratory Manual, 2nd Edition, Cold Spring Harbor Laboratory Press, (1989)).

Although it is possible to use unamplified nucleic acid, due to the relative scarcity of nucleic acid in an HIV-1 sample it is preferable to amplify it. Nucleic acid may be selectively amplified using the technique of polymerase chain reaction (PCR), which is an in vitro method for producing large amounts of specific nucleic acid fragment of defined length and sequence from small amounts of a template.

The PCR is comprised of standard reactants using $Mg^{2+}$ concentration, oligonucleotide primers and temperature cycling conditions for amplification of the RT gene using the primers. The primers are chosen such that they will amplify the entire RT gene or a selected sequence which incorporates nucleotides corresponding to a region of the wild-type DNA sequence of HIV-1 that includes the codon which is mutated.

RNA cannot be amplified directly by PCR. Its corresponding cDNA must be synthesized. Synthesis of cDNA is normally carried out by primed reverse transcription using oligo-dT primers. Advantageously, primers are chosen such that they will simplify the nucleic acid sequence for RT or a selected sequence which incorporates nucleotides corresponding to the region of RNA corresponding to the wild-type DNA sequence or to the region of the mutant DNA sequence corresponding to the 70th (K to N), 90th or 172th codon of the reverse transcriptase region. This could be achieved by preparing an oligonucleotide primer which is complementary to a region of the RNA strand which is upstream of the corresponding sequence of the wild-type DNA sequence. cDNA prepared by this methodology (see Maniatis, T., et al., supra.) can then be used in the same way as for the DNA already discussed.

The next stage of the methodology is to hybridize to the nucleic acid an oligonucleotide which is complementary to a region of the wild-type DNA sequence (or its corresponding RNA) or to a region of the mutant DNA sequence (or its corresponding RNA).

Conditions and reagents are then provided to permit polymerization of the nucleic acid from the 3'-end of the oligonucleotide primer. Such polymerization reactions are well-known in the art.

If the oligonucleotide primer has at its 3'-end a nucleotide which is complementary to a mutant genotype, that is a genotype which has a nucleotide change at the 70th (K to N), 90th or 172th codon in the RT region, then polymerization of the nucleic acid sequence will only occur if the nucleic acid of the sample is the same as the mutant genotype. Polymerization of a wild type nucleic acid sequence will not occur or at least not to a significant extent because of a mis-match of nucleotides at the 3'-end of the oligonucleotide primer and the nucleic acid sequence of the sample.

If the oligonucleotide primer has at its 3'-end of nucleotide which is complementary to the wild-type genotype, that is a genotype which has the wild-type nucleotide at the 70th (K to N), 90th or 172th codon in the RT region, then there will be polymerization of a nucleic acid sequence which is wild-type at that position. There will be no polymerization of a nucleic acid which has a mutant nucleotide at the 3'-position.

The preferred length of each oligonucleotide is 15–20 nucleotides. The oligonucleotide can be prepared according to methodology well known to the man skilled in the art (Koster, H., Drug Research, 30 p548 (1980); Koster, H., Tetrahedron Letters p1527 (1972); Caruthers, Tetrahedron Letters, p719, (1980); Tetrahedron Letters, p1859, (1981); Tetrahedron Letters 24, p245, (1983); Gate. M. Nucleic Acid Research, 8, p1081, (1980)) and is generally prepared using an automated DNA synthesizer such as an Applied Biosystems 381A synthesizer.

It is convenient to determine the presence of an oligonucleotide primer extended product. The means for carrying out the detection is by using an appropriate label.

The label may be conveniently attached to the oligonucleotide primer or to some other molecule which will bind the primer extended polymerization product.

The label may be for example an enzyme, radioisotope or fluorochrome. A preferred label may be biotin which could be subsequently detected using streptavidin conjugated to an enzyme such as peroxidase or alkaline phosphatase. The presence of an oligonucleotide primer extended polymerization product can be detected for example by running the polymerization reaction on an agarose gel and observing a specific DNA fragment labeled with ethidium bromide, or Southern blotted and autoradiographed to detect the presence or absence of bands corresponding to polymerised product. If a predominant band is present which corresponds only to the labeled oligonucleotide then this indicates that polymerization has been occurred. If bands are present of the correct predicted size, this would indicate that polymerization has occurred.

For example, DNA isolated from patients' lymphocytes as described herein is used as a template for PCR amplification using synthetic oligonucleotide primers which either match or mis-match with the amplified sequences. The feasibility of PCR in detecting such mutations has already been demonstrated. PCR using the Amplification Refractory Mutation system ("ARMS") (Newton, C. R., et al. Nucleic Acids Research, 17, p2503, (1989)) Synthetic oligonucleotide are produced that anneal to the regions adjacent to an including the specific mutations such that the 3'ENDE of the oligonucleotide either matches of mismatches with a mutant or wild-type sequence. PCR is carried out which results in the identification of a DNA fragment (using gel electrophoresis) where a match has occurred or no fragment where a mismatch occurred.

DNA is extracted from HIV-1 infected T-cells as described herein and subjected to "ARMS" PCR analysis using these primers.

The presence of a fragment is identified by using an oligonucleotide primer as described above, i.e., by attempting polymerisation using an oligonucleotide primer which may be labeled for the amplified DNA fragment under stringent conditions which only allow hybridization of complementary DNA (the only difference is that differential hybridization does not have to be performed as fragments of DNA amplified by the "ARMS" method will be the same whether derived from mutant or wild-type DNS, so a common oligonucleotide can be used to detect the presence of these fragments. The sequence of such an oligonucleotide is derived from a DNA sequence within the DNA fragment that is conserved amongst HIV-1 strains).

The above PCR assay may be adapted to enable direct detection of mutations associated with D-D4FC resistance in DNA from PBL samples from infected individuals that have not been cultured to obtain virus. As this material generally contains considerably less HIV-1 DNA than that in infected lymphoid cultures a "double PCR" (or nested set) protocol can be used (Simmonds, P., Balfe, P, Peutherer, J. F., Ludlam, C. A., Bishop, J. O. and Leigh Brown, A. J., J. Virol., 64, 864–872, (1990)) to boost the amount of target HIV-1 RT DNA signal in the samples. The double PCR overcomes the problem of limited amplification of a rare template sequence. A small amount of the pre-amplified material may be used in the second PCR with primer pairs designed to allow discrimination of wild type and mutant residues.

A suitable test kit for use in an assay to determine the resistance status of an HIV-1 sample to D-D4FC which makes use of a methodology according to the first aspect of the invention, comprises an oligonucleotide being complementary to a region of the wild-type DNA sequence (or its corresponding RNA) or to a region of the mutant DNA sequence as described herein, other materials required for polymerisation of the nucleic acid from the 3'-end of the oligonucleotide and means for determining the presence of an oligonucleotide primer extended product. Such other materials include appropriate enzymes, buffers and washing solutions, and a label and a substrate for the label if necessary. If PCR is used to amplify nucleic acid then additional materials such as appropriate oligonucleotide primers which will amplify a region of the wild-type DNA sequence (or its corresponding RNA) or a region of the mutant DNA sequence as described herein (or its corresponding RNA) and dNTP's should be included.

In a second aspect of the invention there is provided a method of determining the sensitivity of an HIV-1 sample to D-D4FC which comprises:

(i) isolating the nucleic acid from the sample;
(ii) hybridizing the nucleic acid with an oligonucleotide being complementary to a region of the wild-type DNA sequence (or its corresponding RNA) or to a region of the mutant DNA sequence set forth in FIG. 1 (or its corresponding RNA) containing one or more of the nucleotides at the region of the 70th (K to N), 90th or 172th codon in the RT region; and
(iii) ascertaining whether or not any of the resulting hybrids of the oligonucleotide and nucleic acid have complementary nucleotides at one of these positions.

Preferably the oligonucleotide is so designed to form a perfectly matched hybrid with its complement.

Nucleic acid (DNA or RNA) is isolated from a sample by the aforementioned methods as described for the first aspect of the invention.

Similarly, PCR may be used to amplify the RT DNA (or its corresponding RNA) or preferably to amplify a region of the RT DNA (or its corresponding RNA) which incorporates DNA (or its corresponding RNA) containing one or more of the nucleotides at the designated position.

In the second stage of this methodology the nucleic acid is then used to hybridize to oligonucleotides complementary to a region of the wild-type DNA sequence (or its corresponding (RNA) or to a region of the mutant DNA sequence.

The oligonucleotide may be of any length depending on the number of nucleotide positions of interest which are being examined. If the oligonucleotide is designed to include a nucleotide at only one position of interest then this nucleotide is preferably at or close to the center position of the oligonucleotide.

In order to ascertain whether or not the oligonucleotide and nucleic acid sequence have formed a matched hybrid, specific hybridization conditions are set so that a hybrid is only formed when the nucleotide or nucleotides at the 70th (K to N), 90th or 172th codon of the reverse transcriptase region are complementary to the corresponding nucleotide or nucleotides of the oligonucleotide which either permits hybridization or no hybridization. It is important to establish for example the temperature of the reaction and the concentration of salt solution before carrying out the hybridization step to find conditions that are stringent enough to guarantee specificity (Maniatis, T., et al., Molecular Cloning, A Laboratory Manual, 2nd edition, Cold Spring Harbour Laboratory Press, (1989). If the oligonucleotide probe has a DNA sequence which is complementary to a wild-type nucleic acid sequence at one or more of its nucleotides corresponding to the 70th (K to N), 90th or 172th codon in the reverse transcriptase region then this oligonucleotide will hybridize perfectly to wild-type nucleic acid. If there is no hybridize perfectly to wild-type nucleic acid. If there is no hybridization then this would suggest that the nucleic acid isolated from the same contains one or more mutations.

If the oligonucleotide probe has a DNA sequence which is complementary to a mutant nucleic acid sequence then this oligonucleotide will hybridize to mutant nucleic acid. If there is no hybridization this would suggest that the nucleic acid isolated from the sample contains no such mutation or mutations. The oligonucleotide probes may be labeled as a means of detection as for the first aspect of the invention.

The hybridization and subsequent removal of non-hybridized nucleic acids are performed under stringent conditions which only allow hybridization of the complementary DNA and not the oligonucleotide containing a mismatch (i.e. oligonucleotide specific hybridization as described for the detection of sickle cell mutation using the β-globin or HLA-DQα gene (Saikt, R. K., et al., Nature, 324, p163, (1986), the activated Ras gene (Ver Laan-de, Vries, M., et al., Gene, 50, 313, (1986)) and β-thalassaemia Wong, C., et al., Nature, 330, p384, (1987)).

The hybridization may be carried out by immobilization of the RT nucleic acid sequence onto nitrocellulose, nylon or other solid matrix (e.g. dot-blot). It is convenient to determine the presence of an hybrid by using the means of a label. For example, the chemically synthesized oligonucleotide probes can be suitably labeled using enzyme, radioisotope or fluorochrome. A preferred label may be biotin which could be subsequently detected using streptavidin conjugated to an enzyme such as peroxidase or alkaline phosphatase.

Alternatively the hybridization may be carried out by immobilization of the chemically synthesized oligonucleotides referred to above, which are unlabeled, onto a solid support referred to above and subsequent hybridization by a labeled RT nucleic acid sequence as described previously.

In both situations described above for hybridization suitable control reactions will be incorporated to determine that efficient hybridization has occurred. (e.g., the hybridization of oligonucleotides to a complementary oligonucleotide).

Results would be readily interpreted as the isolated nucleic acid would hybridize to either the wild type oligonucleotide or the mutant oligonucleotide.

A suitable test kit for use in an assay to determine the sensitivity of an HIV-1 sample to D-D4FC which makes use of a methodology according to the second aspect of the invention comprises an oligonucleotide being complementary to a region of the wild-type DNA sequence (or its corresponding RNA) or to the pertinent region of the mutant DNA sequence, along with other materials required to permit hybridization. Such materials include appropriate buffers and washing solutions and a label and a substrate for the label if necessary. Normally the oligonucleotide would be labeled. If PCR is used to amplify nucleic acid prior to hybridization then additional materials such as appropriate oligonucleotide primers which will amplify a region of the wild-type DNA sequence (or its corresponding RNA) or a region of the mutant DNA sequence, appropriate enzymes and dNTP's (deoxy nucleotide triphosphates) should be included.

In one alternate format of the assay, the dNTP's in the amplification may or may not be coupled to a detector molecule such as a radioisotope, biotin, fluorochrome or enzyme.

It is also possible to detect zidovudine resistant mutations in the HIV-1 RT RNA isolated from clinical samples using an RNA amplification system. Using the methodology described by Guatelli et al. (Proc. Natl. Acad. Sci, (USA), 8/7, 1874–1878, (March 1990)) a target nucleic acid sequence can be replicated (amplified) exponentially in vitro under isothermal conditions by using three enzymatic activities essential to retroviral replication: reverse transcriptase, RNase H and a DNA-dependant RNA polymerase. Such a methodology may be employed followed by an hybridization step to distinguish mutant from wild-type nucleotides at discussed previously.

Preparation of Pharmaceutical Compositions

Humans suffering from effects caused by any of the diseases described herein, and in particular, HIV infection, can be treated by administering to the patient an effective amount of D-D4FC or a pharmaceutically acceptable salt or prodrug thereof in the presence of a pharmaceutically acceptable carrier or diluent, for any of the indications or modes of administration as described in detail herein. The active materials can be administered by any appropriate route, for example, orally, parenterally, enterally, intravenously, intradermally, subcutaneously, transdermally, intranasally or topically, in liquid or solid form.

The active compound(s) are included in the pharmaceutically acceptable carrier or diluent in an amount sufficient to deliver to a patient a therapeutically effective amount of compound to inhibit viral replication in vivo, especially HIV replication, without causing serious toxic effects in the treated patient. By "inhibitory amount" is meant an amount of active ingredient sufficient to exert an inhibitory effect as measured by, for example, an assay such as the ones described herein.

A preferred dose of the compound for all the above-mentioned conditions will be in the range from about 1 to 75 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art.

The compounds are conveniently administered in unit any suitable dosage form, including but not limited to one containing 7 to 3000 mg, preferably 70 to 1400 mg of active ingredient per unit dosage form. An oral dosage of 50 to 1000 mg is usually convenient.

Ideally, the active ingredient should be administered to achieve peak plasma concentrations of the active compound of from about 0.02 to 70 micromolar, preferably about 0.5 to 10 mM. This may be achieved, for example, by the intravenous injection of a 0.1 to 25% solution of the active ingredient, optionally in saline, or administered as a bolus of the active ingredient.

The concentration of active compound in the drug composition will depend on absorption, distribution, metabolism and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible bind agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, chewing gum or the like. A syrup may contain, in addition to the active compounds, sucrose as a sweetening agent and certain preservatives, dyes and colorings and flavors.

The compounds or their pharmaceutically acceptable derivative or salts thereof can also be mixed with other active materials that do not impair the desired action, or with materials that supplement the desired action, such as antibiotics, antifungals, antiinflammatories, protease inhibitors, or other nucleoside or non-nucleoside antiviral agents, as discussed in more detail above. Solutions or suspensions used for parental, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Liposomal suspensions (including liposomes targeted to infected cells with monoclonal antibodies to viral antigens) are also preferred as pharmaceutically acceptable carriers, these may be prepared according to methods known to those skilled in the art, for example, as described in U.S. Patent No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Controlled Release Formulations

All of the U.S. patents cited in this section on controlled release formulations are incorporated by reference in their entirety.

The field of biodegradable polymers has developed rapidly since the synthesis and biodegradability of polylactic acid was reported by Kulkarni et al., in 1966 ("Polylactic acid for surgical implants," *Arch. Surg.*, 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), and U.S. Pat. No. 4,530,840 to Tice, et al. (polylactide, polyglycolide, and copolymers). See also U.S. Pat. No. 5,626,863 to Hubbell, et al which describes photopolymerizable biodegradable hydrogels as tissue contacting materials and controlled release carriers (hydrogels of polymerized and crosslinked macromers comprising hydrophilic oligomers having biodegradable monomeric or oligomeric extensions, which are end capped monomers or oligomers capable of polymerization and crosslinking); and PCT WO 97/05185 filed by Focal, Inc. directed to multiblock biodegradable hydrogels for use as controlled release agents for drug delivery and tissue treatment agents.

Degradable materials of biological origin are well known, for example, crosslinked gelatin. Hyaluronic acid has been crosslinked and used as a degradable swelling polymer for biomedical applications (U.S. Pat. No. 4,957,744 to Della Valle et. al.; (1991) "Surface modification of polymeric biomaterials for reduced thrombogenicity," *Polym. Mater. Sci. Eng.*, 62:731–735]).

Many dispersion systems are currently in use as, or being explored for use as, carriers of substances, particularly biologically active compounds. Dispersion systems used for pharmaceutical and cosmetic formulations can be categorized as either suspensions or emulsions. Suspensions are defined as solid particles ranging in size from a few manometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses a method for forming an implant in situ by dissolving a nonreactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

A number of patents disclose drug delivery systems that can be used to administer D-D4FC or a nucleotide or other defined prodrug thereof. U.S. Pat. No. 5,749,847 discloses a method for the delivery of nucleotides into organisms by electrophoration. U.S. Pat. No. 5,718,921 discloses microspheres comprising polymer and drug dispersed therewithin. U.S. Pat. No. 5,629,009 discloses a delivery system for the controlled release of bioactive factors. U.S. Pat. No, 5,578,325 discloses nanoparticles and microparticles of non-linear hydrophilic hydrophobic multiblock copolymers. U.S. Pat. No. 5,545,409 discloses a delivery system for the controlled release of bioactive factors. U.S. Pat. No. 5,494,682 discloses ionically cross-linked polymeric microcapsules.

U.S. Pat. No. 5,728,402 to Andrx Pharmaceuticals, Inc. describes a controlled release formulation that includes an internal phase which comprises the active drug, its salt or prodrug, in admixture with a hydrogel forming agent, and an external phase which comprises a coating which resists dissolution in the stomach. U.S. Pat. Nos. 5,736,159 and 5,558,879 to Andrx Pharmaceuticals, Inc. discloses a controlled release formulation for drugs with little water solubility in which a passageway is formed in situ. U.S. Pat. No. 5,567,441 to Andrx Pharmaceuticals, Inc. discloses a once-a-day controlled release formulation. U.S. Pat. No. 5,508,040 discloses a multiparticulate pulsatile drug delivery system. U.S. Pat. No. 5,472,708 discloses a pulsatile particle based drug delivery system. U.S. Pat. No. 5,458,888 describes a controlled release tablet formulation which can be made using a blend having an internal drug containing phase and an external phase which comprises a polyethylene glycol polymer which has a weight average molecular weight of from 3,000 to 10,000. U.S. Pat. No. 5,419,917 discloses methods for the modification of the rate of release of a drug form a hydrogel which is based on the use of an effective amount of a pharmaceutically acceptable ionizable compound that is capable of providing a substantially zero-order release rate of drug from the hydrogel. U.S. Pat. No. 5,458,888 discloses a controlled release tablet formulation.

U.S. Pat. No. 5,641,745 to Elan Corporation, plc discloses a controlled release pharmaceutical formulation which comprises the active drug in a biodegradable polymer to form microspheres or nanospheres. The biodegradable polymer is suitably poly-D,L-lactide or a blend of poly-D,L-lactide and poly-D,L-lactide-co-glycolide. U.S. Pat. No. 5,616,345 to Elan Corporation plc describes a controlled absorption formulation for once a day administration that includes the active compound in association with an organic acid, and a multi-layer membrane surrounding the core and containing a major proportion of a pharmaceutically acceptable film-forming, water insoluble synthetic polymer and a minor proportion of a pharmaceutically acceptable film-forming water soluble synthetic polymer. U.S. Pat. No. 5,641,515 discloses a controlled release formulation based on biodegradable nanoparticles. U.S. Pat. No. 5,637,320 discloses a controlled absorption formulation for once a day administration. U.S. Pat. Nos. 5,580,580 and 5,540,938 are directed to formulations and their use in the treatment of neurological diseases. U.S. Pat. No. 5,533,995 is directed to a passive transdermal device with controlled drug delivery. U.S. Pat. No. 5,505,962 describes a controlled release pharmaceutical formulation.

Prodrug Formulations

D-D4FC or any of the nucleosides or other compounds which are described herein for use in combination or alternation therapy with D-D4FC or its related compounds can be administered as an acylated prodrug or a nucleotide prodrug, as described in detail below.

Any of the nucleosides described herein or other compounds that contain a hydroxyl or amine function can be administered as a nucleotide prodrug to increase the activity, bioavailability, stability or otherwise alter the properties of the nucleoside. A number of nucleotide prodrug ligands are known. In general, alkylation, acylation or other lipophilic modification of the hydroxyl group of the compound or of the mono, di or triphosphate of the nucleoside will increase the stability of the nucleotide. Examples of substituent groups that can replace one or more hydrogens on the phosphate moiety or hydroxyl are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides or other compounds to achieve a desire effect.

The active nucleoside or other hydroxyl containing compound can also be provided as an ether lipid (and particularly a 5'-ether lipid for a nucleoside), as disclosed in the following references, Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses.* 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine." *Antimicrob. Agents Chemother.* 36:2025.2029; Hostetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside or other hydroxyl or amine containing compound, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No.

5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et-al.), Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Nonlimiting examples of nucleotide prodrugs are described in the following references: Ho, D. H. W. (1973) "Distribution of Kinase and deaminase of 1β-D-arabinofuranosylcytosine in tissues of man and muse." Cancer Res. 33, 2816–2820; Holy, A. (1993) Isopolar phosphorous-modified nucleotide analogues," In: De Clercq (Ed.), Advances in Antiviral Drug Design, Vol. I, JAI Press, pp. 179–231; Hong, C. I., Nechaev, A., and West, C. R. (1979a) "Synthesis and antitumor activity of 1β-D-arabino-furanosylcytosine conjugates of cortisol and cortisone." Biochem. Biophys. Rs. Commun. 88, 1223–1229; Hong, C. I., Nechaev, A., Kirisits, A. J. Buchheit, D. J. and West, C. R. (1980) "Nucleoside conjugates as potential antitumor agents. 3. Synthesis and antitumor activity of 1-(β-D-arabinofuranosyl)cytosine conjugates of corticosteroids and selected lipophilic alcohols." J. Med. Chem. 28, 171–177; Hostetler, K. Y., Stuhmiller, L. M., Lenting, H. B. M. van den Bosch, H. and Richman J Biol. Chem. 265, 6112–6117; Hostetler, K. Y., Carson, D. A. and Richman, D. D. (1991); "Phosphatidylazidothymidine: mechanism of antiretroviral action in CEM cells." J. Biol Chem. 266, 11714–11717; Hostetler, K. Y., Korba, B. Sridhar, C., Gardener, M. (1994a) "Antiviral activity of phosphatidyl-dideoxycytidine in hepatitis B-infected cells and enhanced hepatic uptake in mice." Antiviral Res. 24, 59–67; Hostetler, K. Y., Richman, D. D., Sridhar. C. N. Felgner, P. L. Felgner, J., Ricci, J., Gardener, M. F. Selleseth, D. W. and Ellis, M. N. (1994b) "Phosphatidylazidothymidine and phosphatidyl-ddC: Assessment of uptake in mouse lymphoid tissues and antiviral activities in human immunodeficiency virus-infected cells and in rauscher leukemia virus-infected mice." Antimicrobial Agents Chemother. 38, 2792–2797; Hunston, R. N., Jones, A. A. McGuigan, C., Walker, R. T., Balzarini, J., and DeClercq, E. (1984) "Synthesis and biological properties of some cyclic phosphotriesters derived from 2'-deoxy-5-fluorouridine." J. Med. Chem. 27,440–444; Ji, Y. H., Moog, C., Schmitt, G., Bischoff, P. and Luu, B. (1990); "Monophosphoric acid esters of 7-β-hydroxycholesterol and of pyrimidine nucleoside as potential antitumor agents: synthesis and preliminary evaluation of antitumor activity." J. Med. Chem. 33 2264–2270; Jones, A. S., McGuigan, C., Walker, R. T., Balzarini, J. and DeClercq, E. (1984) "Synthesis, properties, and biological activity of some nucleoside cyclic phosphoramidates." J. Chem. Soc. Perkin Trans. I, 1471–1474; Juodka, B. A. and Smart, J. (1974) "Synthesis of diribonucleoside phosph (P→N) amino acid derivatives." Coll. Czech. Chem. Comm. 39, 363–968; Kataoka, S., Imai, J., Yamaji, N., Kato, M., Saito, M., Kawada, T. and Imai, S. (1989) "Alkylated cAMP derivatives; selective synthesis and biological activities." Nucleic Acids Res. Sym. Ser. 21, 1–2; Kataoka, S., Uchida, "(cAMP) benzyl and methyl triesters." Heterocycles 32, 1351–1356; Kinchington, D., Harvey, J. J., O'Connor, T. J., Jones, B. C. N. M., Devine, K. G., Taylor-Robinson D., Jeffries, D. J. and McGuigan, C. (1992) "Comparison of antiviral effects of zidovudine phosphoramidate and phosphorodiamidate derivatives against HIV and ULV in vitro." Antiviral Chem. Chemother. 3, 107–112; Kodama, K., Morozumi, M., Saithoh, K. I., Kuninaka, H., Yosino, H. and Saneyoshi, M. (1989) "Antitumor activity and pharmacology of 1-β-D-arabinofuranosylcytosine -5'-stearylphosphate; an orally active derivative of 1-β-Darabinofuranosylcytosine." Jpn. J. Cancer Res. 80, 679–685; Korty, M. and Engels, J. (1979) "The effects of adenosine- and guanosine 3',5' phosphoric and acid benzyl esters on guinea-pig ventricular myocardium." Naunyn-Schmiedeberg's Arch. Pharmacol. 310, 103–111; Kumar, A., Goe, P. L., Jones, A. S. Walker, R. T. Balzarini, J. and DeClercq, E. (1990) "Synthesis and biological evaluation of some cyclic phosphoramidate nucleoside derivatives." J. Med. Chem, 33, 2368–2375; LeBec, C., and Huynh-Dinh, T. (1991) "Synthesis of lipophilic phosphate triester derivatives of 5-fluorouridine an arabinocytidine as anticancer prodrugs." Tetrahedron Lett. 32, 6553–6556; Lichtenstein, J., Barner, H. D. and Cohen, S. S. (1960) "The metabolism of exogenously supplied nucleotides by Escherichia coli.," J. Biol. Chem. 235, 457–465; Lucthy, J., Von Daeniken, A., Friederich, J. Manthey, B., Zweifel, J., Schlatter, C. and Benn, M. H. (1981) "Synthesis and toxicological properties of three naturally occurring cyanoepithioalkanes". Mitt. Geg. Lebensmittelunters. Hyg. 72, 131–133 (Chem. Abstr. 95, 127093); McGigan, C. Tollerfield, S. M. and Riley, P. a. (1989) "Synthesis and biological evaluation of some phosphate triester derivatives of the anti-viral drug Ara." Nucleic Acids Res. 17, 6065–6075; McGuigan, C., Devine, K. G., O'Connor, T. J., Galpin, S. A., Jeffries, D. J. and Kinchington, D. (1990a) "Synthesis and evaluation of some novel phosphoramidate derivatives of 3'-azido-3'-deoxythymidine (AZT) as anti-HIV compounds." Antiviral Chem. Chemother. 1 107–113; McGuigan, C., O'Connor, T. J., Nicholls, S. R. Nickson, C. and Kinchington, D. (1990b) "Synthesis and anti-HIV activity of some novel substituted dialkyl phosphate derivatives of AZT and ddCyd." Antiviral Chem. Chemother. 1, 355–360; McGuigan, C., Nicholls, S. R., O'Connor, T. J., and Kinchington, D. (1990c) "Synthesis of some novel dialkyl phosphate derivative of 3'-modified nucleosides as potential anti-AIDS drugs." Antiviral Chem. Chemother. 1, 25–33; McGuigan, C., Devin, K. G., O'Connor, T. J., and Kinchington, D. (1991) "Synthesis and anti-HIV activity of some haloalkyl phosphoramidate derivatives of 3'-azido-3'deoxythylmidine (AZT); potent activity of the trichloroethyl methoxyalaninyl compound." Antiviral Res. 15, 255–263; McGuigan, C., Pathirana, R. N., Balzarini, J. and DeClercq, E. (1993b) "Intracellular delivery of bioactive AZT nucleotides by aryl phosphate derivatives of AZT." J. Med. Chem. 36, 1048–1052.

Alkyl hydrogen phosphate derivatives of the anti-HIV agent AZT may be less toxic than the parent nucleoside analogue. Antiviral Chem. Chemother. 5, 271–277; Meyer, R. B., Jr., Shuman, D. A. and Robins, R. K. (1973) "Synthesis of purine nucleoside 3',5'-cyclic phosphoramidates." Tetrahedron Lett. 269–272; Nagyvary, J. Gohil, R. N., Kirchner, C. R. and Stevens, J. D. (1973) "Studies on neutral esters of cyclic AMP," Biochem. Biophys. Res. Commun. 55, 1072–1077; Namane, A. Gouyette, C., Fillion, M. P., Fillion, G. and Huynh-Dinh, T. (1992) "Improved brain delivery of AZT using a glycosyl phosphotriester prodrug." J. Med. Chem. 35, 3039–3044; Nargeot, J. Nerbonne, J. M. Engels, J. and Leser, H. A. (1983) Natl. Acad. Sci. U.S.A. 80, 2395–2399; Nelson, K. A., Bentrude, W. G. Stser, W. N. and Hutchinson, J. P. (1987) "The question of chair-twist equilibria for the phosphate rings of nucleoside cyclic 3',5'monophosphates. $^1$HNMR and x-ray crystallographic study of the diastereomers of thymidine phenyl cyclic 3',5'-monophosphate." *J. Am. Chem. Soc.* 109, 4058–4064; Nerbonne, J. M., Richard, S., Nargeot, J. and Lester, H. A. (1984) "New photoactivatable cyclic nucleotides produce intracellular jumps in cyclic AMP and cyclic GMP concentrations." *Nature* 301, 74–76; Neumann, J. M., Herv_, M., Debouzy, J. C., Guerra, F. I., Gouyette, C., Dupraz, B. and Huyny-Dinh, T. (1989) "Synthesis and transmembrane transport studies by NMR of a glucosyl phospholipid of thymidine." *J. Am. Chem. Soc.* 111, 4270–4277; Ohno, R., Tatsumi, N., Hirano, M., Imai, K. Mizoguchi, H., Nakamura, T., Kosaka, M., Takatuski, K., Yamaya, T., Toyama K., Yoshida, T., Masaoka, T., Hashimoto, S., Ohshima, T., Kimura, I., Yamada, K. and Kimura, J. (1991) "Treatment of myelodysplastic syndromes with orally administered 1-β-D-arabinouranosylcytosine -5' stearylphosphate." *Oncology* 48, 451–455. Palomino, E., Kessle, D. and Horwitz, J. P. (1989) "A dihydropyridine carrier system for sustained delivery of 2',3' dideoxynucleosides to the brain." *J. Med. Chem.* 32, 22–625; Perkins, R. M., Barney, S. Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) "Activity of BRL47923 and its oral prodrug, SB203657A against a rauscher murine leukemia virus infection in mice." *Antiviral Res.* 20 (Suppl. 1). 84; Piantadosi, C., Marasco, C. J., Jr., Norris-Natschke, S. L., Meyer, K. L., Gumus, F., Surles, J. R., lshaq, K. S., Kucera, L. S. Iyer, N., Wallen, C. A., Piantadosi, S. and Modest, E. J. (1991) "Synthesis and evaluation of novel ether lipid nucleoside conjugates for anti-HIV-1 activity." *J. Med. Chem.* 34, 1408–1414; Pompon, A., Lefebvre, I., Imbach, J. L., Kahn, S. and Farquhar, D. (1994). "Decomposition pathways of the mono- and bis(pivaloyloxymethyl) esters of azidothymidine-5'-monophosphate in cell extract and in tissue culture medium; an application of the 'on-line ISRP-cleaning HPLC technique." *Antiviral Chem Chemother.* 5, 91–98; Postemark, T. (1974) "Cyclic AMP and cyclic GMP." *Annu. Rev. Pharmacol.* 14, 23–33; Prisbe, E. J., Martin, J. C. M., McGhee, D. P. C., Barker, M. F., Smee, D. F. Duke, A. E., Matthews, T. R. and Verheyden, J. P. J. (1986) "Synthesis and antiherpes virus activity of phosphate an phosphonate derivatives of 9-[(1, 3-dihydroxy-2-propoxy)methyl]guanine. " *J. Med. Chem.* 29, 671–675; Pucch, F., Gosselin, G., Lefebvre, I., Pompon, a., Aubertin, A. M. Dim, and Imbach, J. L. (1993) "Intracellular delivery of nucleoside monophosphate through a reductase-mediated activation process." *Antiviral Res.* 22, 155–174; Pugaeva, V. P., Klochkeva, S. I., Mashbits, F. D. and Eizengart, R. S. (1969). "Toxicological assessment and health standard ratings for ethylene sulfide in the industrial atmosphere." *Gig. Trf. Prof. Zabol.* 14, 47–48 (*Chem. Abstr.* 72, 212); Robins, R. K. (1984) "The potential of nucleotide analogs as inhibitors of Retro viruses and tumors." *Pharm. Res.* 11–18; Rosowsky, A., Kim. S. H., Ross and J. Wick, M. M. (1982) "Lipophilic 5'-(alkylphosphate) esters of 1-β-D-arabinofiiranosylcytosine and its $N^4$-acyl and 2.2'-anhydro-3'-O-acyl derivatives as potential prodrugs." *J. Med. Chem.* 25, 171–178; Ross, W. (1961) "Increased sensitivity of the walker turnout towards aromatic nitrogen mustards carrying basic side chains following glucose pretreatment." *Biochem. Pharm.* 8, 235–240; Ryu, E. K., Ross, R. J. Matsushita, T., MacCoss, M., Hong, C. I. and West, C. R. (1982). "Phospholipid-nucleoside conjugates. 3. Synthesis and preliminary biological evaluation of 1-β-D-arabinofuranosylcytosine 5'diphosphate [–], 2-diacylglycerols." *J. Med. Chem.* 25, 1322–1329; Saffhill, R. and Hume, W. J. (1986) "The degradation of 5-iododeoxyuridine and 5-bromoethoxyuridine by serum from different sources and its consequences for the use of these compounds for incorporation into DNA." *Chem. Biol. Interact.* 57, 347–355; Saneyoshi, M., Morozumi, M., Kodama, K., Machida, J., Kuninaka, A. and Yoshino, H. (1980) "Synthetic nucleosides and nucleotides. XVI. Synthesis and biological evaluations of a series of 1-β-D-arabinofuranosylcytosine 5'-alky or arylphosphates." *Chem Pharm. Bull.* 28, 2915–2923; Sastry, J. K., Nehete, P. N., Khan, S., Nowak, B. J., Plunkett, W., Arlinghaus, R. B. and Farquhar, D. (1 992) "Membrane-permeable dideoxyuridine 5'-monophosphate analogue inhibits human immunodeficiency virus infection." *Mol. Pharmacol.* 41, 441–445; Shaw, J. P., Jones, R. J. Arimilli, M. N., Louie, M. S., Lee, W. A. and Cundy, K. C. (1994) "Oral bioavailability of PMEA from PMEA prodrugs in male Sprague-Dawley rats." *9th Annual AAPS Meeting*. San Diego, Calif. (Abstract). Shuto, S., Ueda, S., Imamura, S., Fukukawa, K. Matsuda, A. and Ueda, T. (1987) "A facile one-step synthesis of 5' phosphatidiylnucleosides by an enzymatic two-phase reaction." *Tetrahedron Lett.* 28, 199–202; Shuto, S. Itoh, H., Ueda, S., Imamura, S., Kukukawa, K., Tsujino, M., Matsuda, A. and Ueda, T. (1988) *Pharm. Bull.* 36, 209–217. An example of a useful phosphate prodrug group is the S-acyl-2-thioethyl group, also referred to as "SATE".

This invention has been described with reference to its preferred embodiments. Variations and modifications of the invention, will be obvious to those skilled in the art from the foregoing detailed description of the invention. It is intended that all of these variations and modifications be included within the scope of this invention.

We claim:

1. A method for treating an HIV infection in a human comprising administering an effective amount of β-D-D4FC or its pharmaceutically acceptable ester or salt to the human, optionally in a pharmaceutically acceptable carrier, in combination or alternation with an effective amount of abacavir.

2. A pharmaceutical composition comprising an effective amount of β-D-D4FC or its pharmaceutically acceptable ester or salt, in a pharmaceutically acceptable carrier, in combination with an effective amount of abacavir.

3. The method of claim 1, wherein β-D-D4FC and abacavir are administered in a pharmaceutically acceptable carrier.

4. The method according to claim 3, wherein the pharmaceutically acceptable carrier is suitable for oral delivery, intravenous delivery, parenteral delivery, intradermal delivery, subcutaneous delivery or topical delivery.

5. The method of claim 1, wherein β-D-D4FC and abacavir are in the form of a dosage unit.

6. The method of claim 5, wherein the dosage unit contains 10 to 1500 mg of each compound.

7. The method of claim 5, wherein the dosage unit is a tablet or capsule.

8. The method of claim 1 wherein β-D-D4FC and abacavir are administered in combination.

9. The method of claim 1 wherein β-D-D4FC and abacavir are administered in alternation.

10. The pharmaceutical composition according to claim 2, wherein the β-D-D4FC and abacavir are in a pharmaceutically acceptable carrier.

11. The pharmaceutical composition according to claim 10, wherein the pharmaceutically acceptable carrier is suitable for oral delivery, intravenous delivery, parenteral delivery, intradermal delivery, subcutaneous delivery or topical delivery.

12. The pharmaceutical composition according to claim 11, wherein the pharmaceutically acceptable carrier is suitable for oral delivery.

13. The pharmaceutical composition according to claim 11, wherein the pharmaceutically acceptable carrier is suitable for intravenous delivery.

14. The pharmaceutical composition according to claim 11, wherein the pharmaceutically acceptable carrier is suitable for parenteral delivery.

15. The pharmaceutical composition according to claim 11, wherein the pharmaceutically acceptable carrier is suitable for intradermal delivery.

16. The pharmaceutical composition according to claim 11, wherein the pharmaceutically acceptable carrier is suitable for topical delivery.

17. The pharmaceutical composition according to claim 2, wherein β-D-D4FC and abacavir are in the form of a dosage unit.

18. The pharmaceutical composition according to claim 17, wherein the dosage unit contains 10 to 1500 mg of each compound.

19. The pharmaceutical composition according to claim 17, wherein the dosage unit is a tablet or capsule.

* * * * *